United States Patent [19]
Dennis et al.

[11] Patent Number: 5,951,605
[45] Date of Patent: Sep. 14, 1999

[54] METHOD AND APPARATUS FOR HIP PROSTHESIS

[75] Inventors: Douglas A. Dennis; Richard D. Komistek, both of Denver, Colo.

[73] Assignee: Rose Biomedical Research, Denver, Colo.

[21] Appl. No.: 08/672,994

[22] Filed: Jul. 1, 1996

[51] Int. Cl.⁶ .................................................. A61F 2/34
[52] U.S. Cl. ............................................................. 623/23
[58] Field of Search ................................. 623/13, 18, 19, 623/21, 22, 23

[56] References Cited

U.S. PATENT DOCUMENTS

| | | | |
|---|---|---|---|
| 2,765,787 | 10/1956 | Pellet ........................................ | 623/23 |
| 3,658,056 | 4/1972 | Huggler et al. ........................... | 623/23 |
| 5,389,107 | 2/1995 | Nassar et al. ............................. | 623/22 |
| 5,549,691 | 8/1996 | Harwin ...................................... | 623/22 |

*Primary Examiner*—David J. Isabella
*Attorney, Agent, or Firm*—Gibson, Dunn & Crutcher LLP

[57] ABSTRACT

An prosthesis for allowing natural ball and socket type movement, as in a hip or shoulder. A femoral component having a ball at one extremity is engaged with an acetabular component having a hemispherical cup to receive the ball. A ligamentous material extends from a port in the hemispherical cup to a port in the ball to apply a resistive force to resist any dislocating force, the resistive force varying in proportion to the movement of the femoral component from a natural and relaxed position in relation to the acetabular component.

14 Claims, 2 Drawing Sheets

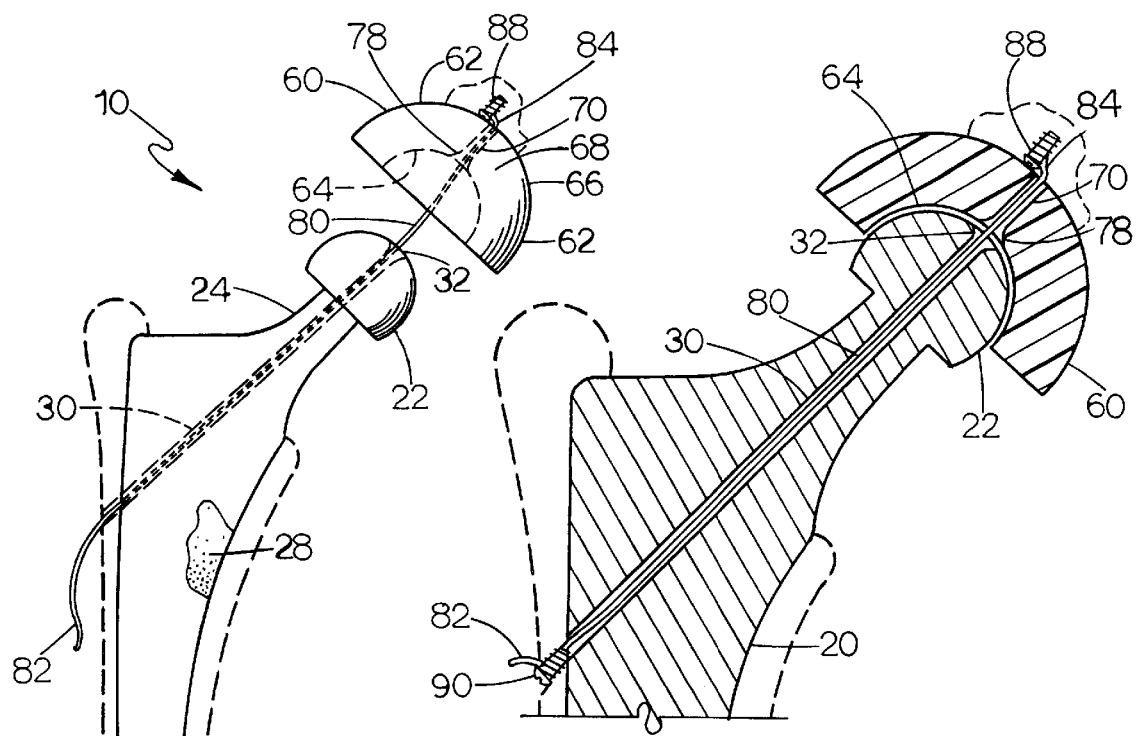
FIG. 1
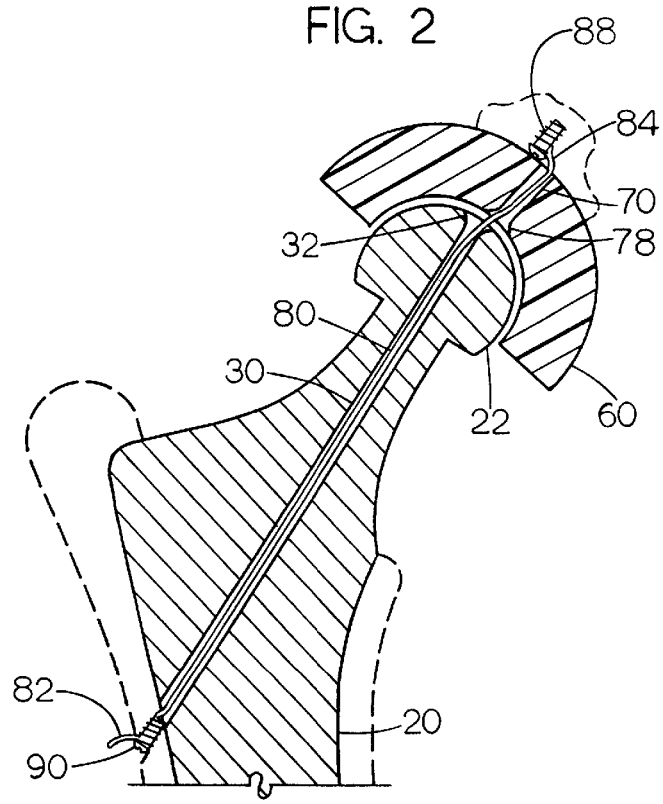
FIG. 2
FIG. 3

METHOD AND APPARATUS FOR HIP PROSTHESIS

FIELD OF THE INVENTION

The present invention relates to a prosthesis, and more particularly to an apparatus and method for engaging the femoral component of a hip prothesis with the acetabular component of the hip prosthesis utilizing a ligamentous attachment extending from the femur through a hole in the femoral stem and femoral head and through the cup of the acetabular component to the acetabulum.

BACKGROUND OF THE INVENTION

Artificial hip and shoulder ball joints conventionally employ ball and socket articulation components. In a hip prosthesis, the acetabular portion is embedded in the bony structure of the acetabulum and the femoral portion is embedded in the femur. The femoral portion normally includes the ball while the acetabular portion normally includes the socket or cup. The ball is attached to an arm composed of a neck which in turn is attached to a stem or shaft.

It has been found in use that a dislocating force is created when the neck of the arm attached to the ball impinges on the rim of the acetabular component. Because of the leverage associated with the patient's femur, the dislocating force produced when the neck contacts the rim of the bearing can be considerable. For example, a force applied to a patient's leg can produce a dislocating force of several fold because of the leverages involved. Unfortunately, as is apparent from the geometry of the situation, the more the socket bearing encompasses the ball, the greater the restraining force on the ball, but at the same time the less the range of motion prior to the neck impinging upon the edge of the bearing to create undesired leverage.

A number of methods are known for retaining the ball in the cup. In the most common method, the patient's own anatomy, i.e., his or her muscles, tendons and ligaments, are used to retain the ball within the socket. A hemispherical cup typically is used which allows the ball and its attached neck the maximum amount of movement without contact of the neck with the edge of the cup. The surgeon when installing such a prosthesis aligns the ball and cup as closely as possible with the patient's natural anatomy so that the patient's movements do not tend to dislocate the ball from the cup. Such precise alignment is easiest the first time the prosthesis is implanted in a patient. Subsequent reconstructions are much more difficult to align because of deterioration of the anatomy as a result of the first operation, the healing process after the operation, the incompetency of soft tissue, and changes in the anatomy caused by the presence of the prosthesis itself.

Notwithstanding the various retaining systems attempted in the prior art, a significant number of prostheses dislocate. Such dislocations immobilize the patient, can be painful, and can necessitate the discomfort and expense of a second operation. As discussed above, the critical alignment is even more difficult to achieve and maintain when a second implantation is performed. Accordingly, even higher dislocation frequencies are encountered for second and subsequent implantations.

An alternative to the semi-constrained construction is a construction wherein the cup is physically constrained. In this construction, a spherically-shaped bearing surrounds the ball and serves as the cup. The bearing is attached to a fixation element which is embedded in, for example, the patient's pelvic bone. The bearing encompasses more than one-half of the ball surface and thus constrains the ball and its attached arm from dislocation. For plastic bearings, the ball and bearing are usually assembled by forcing the bearing over the ball. The more of the ball which is encompassed by the bearing, the greater the required assembly force, and the greater the constraining force to prevent postoperative dislocation of the joint. In addition, the more that the bearing encompasses the ball, the smaller the range of motion for the ball prior to contact of the bearing with the arm attached to the ball. An example of a constrained artificial joint employing a plastic bearing is shown in U.S. Pat. No. 3,996,625 by Noiles.

A constrained construction using a metal socket bearing is shown in U.S. Reissue Pat. No. 28,895 by Noiles. In a practical sense, the metal bearing of Noiles can be said to be non-dislocatable, since the force required to extract the metal sphere from the enclosing metal socket bearing is at least several thousand pounds. Accordingly, in use, rather than the metal ball dislocating from the metal socket bearing, a high dislocating force will cause the fixation element to be disrupted from the bone in which it has been embedded. Metal balls in metal socket bearings are used in only a minority of joint reconstructions.

Another type of artificial ball and socket joint, referred to as an endoprosthesis, eliminates the fixation element associated with the socket and simply uses a ball surrounded by a plastic socket bearing in a spherical metal head, which head is placed in the patient's natural socket but not secured to bone. For this construction, the ball can rotate within the bearing up to the rim of the bearing (the bearing is greater than a hemisphere so as to be retained on the ball), and then the bearing and its attached head rotate in the patient's socket. As with certain other constructions, anatomical alignment is used to avoid dislocations, in this case between the metal head and the natural socket.

A device which is adaptable to employ several different constraining systems is shown in U.S. Pat. No. 4,960,427 by Noiles. Examples of other prostheses are disclosed in U.S. Pat. Nos. 5,314,489 by Hoffman, U.S. Pat. No. 5,201,767 by Caldanse, U.S. Pat. No. 4,778,473 by Mathews, U.S. Pat. No. 5,108,445 by Ashby, U.S. Pat. No. 5,370,704 by DeCarlo and U.S. Pat. No. 5,413,610 by Amino.

SUMMARY OF THE INVENTION

The present invention is an apparatus and method for constraining the ball component and the cup component of a prosthesis. Although the description below is set forth in the context of a hip prosthesis, it will be apparent that the invention is equally applicable to a shoulder prosthesis or any other prosthesis imitative of a ball and socket joint.

The prosthesis of the invention includes a ball which constitutes the femoral head of the femoral component, a femoral neck which is securely attached to the ball either by integral fabrication with the ball or by attachment means, and a femoral stem extending from the neck for implantation within the medullary canal of the femur. The stem preferably includes tissue in-growth surfaces for bone tissue in-growth to facilitate secure attachment of the femoral component of the prosthesis to the femur. The attachment of the femoral component to the femur may or may not utilize cement.

The ball includes a port extending from the interior of the ball through the wall of the ball to the exterior surface of the extreme of the femoral head. Through the port is threaded a natural or artificial ligamentous material such as teflon, polyester, polyethylene, Gortex or other material. It may be autogenous, homologous, xenographic or synthetic, or any combination thereof. The ligamentous material continues from the ball interior through the femoral neck and out a second port in the upper portion of the femoral stem opposite the femoral ball and neck. The femoral end of the ligamentous material can be tied off or otherwise secured on or outside the femoral stem or on the femur itself. Alternatively, the ligamentous material may be fixed at one end in the ball interior.

The cup in the acetabulum component is of a conventional biocompatible cup material used for ball and socket prostheses, such as polyethylene or polished cobalt chromium, and is implanted in the bony structure of the acetabulum of the patient in the conventional manner. The cup includes a cup port to receive the acetabulum end of the ligamentous material, which is threaded through the cup port and tied off or otherwise attached to the exterior surface of the acetabular component or to the bony structure of the acetabulum. The acetabular component is secured to the bony structure of the acetabulum of the patient in the conventional manner utilizing an appropriate combination of cement, fasteners and in-growth surfaces.

The ligamentous material thus extends from the acetabular end which is attached to the acetabulum, through the cup port, through the ball of the femoral head and through the femoral neck interior, and out the femoral stem port where it is tied off or secured to the femur. In a preferred embodiment the port in the femoral ball or the port in the acetabulum cup or both are chamfered on the end which meets the opposite joint component. The chamfering allows the ball to move within the cup without binding the ligamentous material between the ball and cup.

The ligamentous material thus attaches the femur component to the acetabulum. The attachment can be varied from a secure attachment in which there is tension in the ligamentous material in order to maintain close alignment of the ball in the cup while permitting normal universal ball and socket type movement, to a loose attachment in which there is a desired amount of "play" in the ligamentous material in order to allow normal universal ball and socket type movement as well as limited movement of the ball into and out of the cup. The two ends of the ligamentous material can be secured, and the degree of attachment of the femoral component to the acetabular component can therefore be established, either prior to or during the implantation procedure.

In an alternative embodiment, the ligamentous material is wholly on the outer surfaces of the femoral component and acetabular component. The ligamentous material thus includes a femoral end which attaches to the femur and an acetabular end which attaches to the acetabulum. The ligamentous material may comprise a single element or multiple elements arranged in a mesh or other desired configuration.

The play in the ligamentous material, and similarly the pathways for the ligamentous material, can be chosen based on a variety of factors such as patient lifestyle and physiology.

BRIEF DESCRIPTION OF THE DRAWING

FIG. 1 is an elevation view of the preferred embodiment of the invention.

FIG. 2 is a side sectional view of a portion of the invention, shown with the femoral component engaged with the acetabulum component by the ligament.

FIG. 3 is a side sectional view of a portion of the invention, shown with the femoral component shifted with respect to the acetabulum component.

DETAILED DESCRIPTION OF A PREFERRED EMBODIMENT

Figure 4:
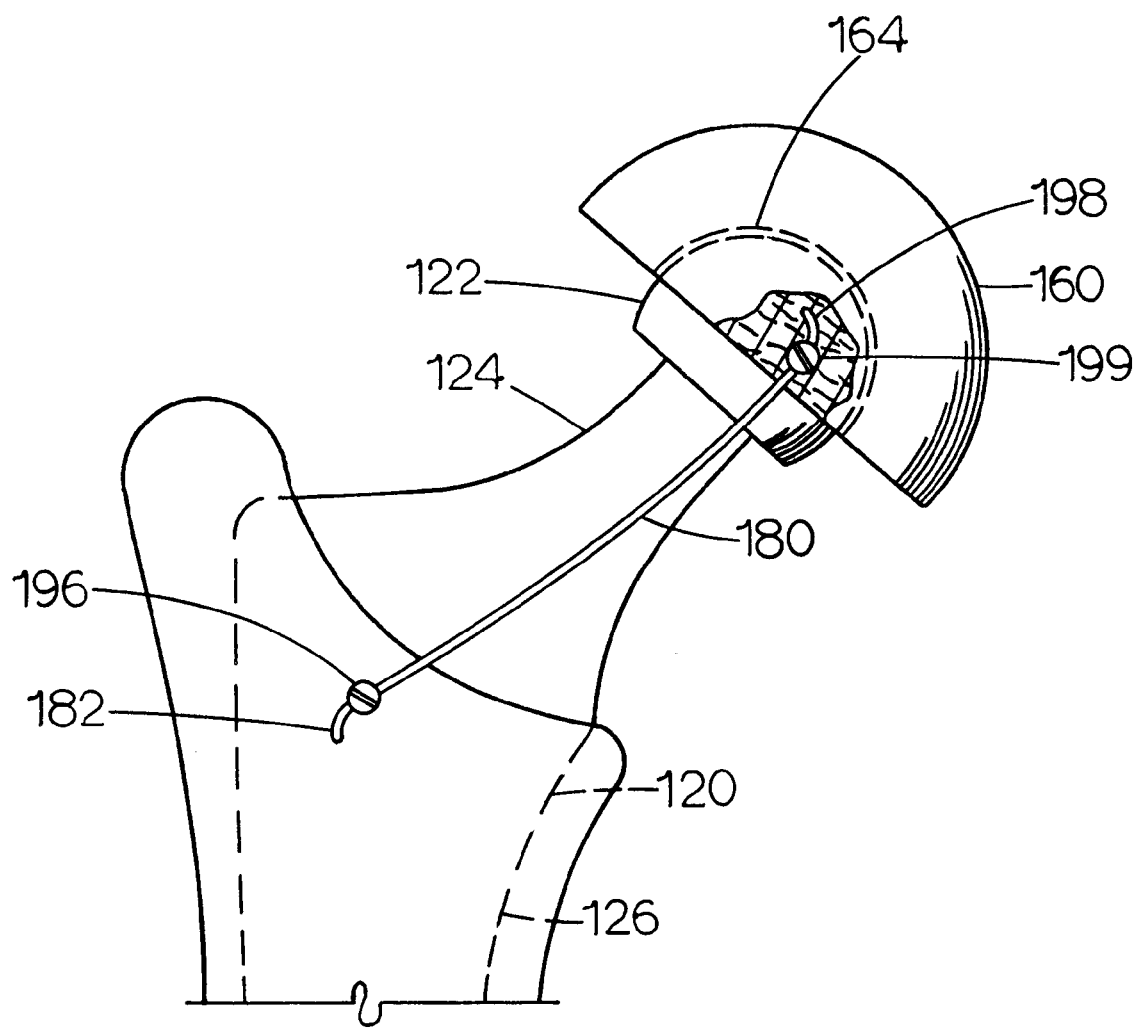
FIG. 4 is an elevation view of an alternative embodiment of the invention.

An elevation view of a preferred embodiment of the invention 10 is depicted in FIG. 1 in which the bone structure of the patient is shown in phantom. A femoral component 20 includes a ball 22 at the femoral extreme, the ball being in the shape of a partial sphere or a hemisphere. The ball is attached to or formed integrally with a neck portion 24 of the femoral component 20, which in turn is attached to or formed integrally with a stem portion 26 of the femoral component 20.

The femoral component 20 is of an overall shape and size that is typical in the field of hip prostheses. In-growth texturing is on the surface of portions of the femoral component 20, illustrative texturing 28 being shown in FIG. 1. The femoral component 20 may or may not be attached to the femur with cement. The femoral component 20 is fabricated in the well-known manner from forged stainless steel or other durable biocompatible material such as titanium or cobalt alloys or alumina or zirconia ceramics. The normal size, shape, material and manufacture of the femoral component of hip prostheses are generally known in the art, and are not further described herein.

The femoral component 20 of the present invention 10 differs from those of the prior art in that a ligament port 30 extends from the femoral component extreme at the ball 22 surface, through the femoral neck 24, and to the surface of femoral stem 26. The preferred embodiment shown in FIG. 1 shows the ligament port 30 as substantially straight, extending radially from the ball 22 surface, through the ball 22 center. However, the ligament port 30 may assume other directions as well, so long as the ball end 32 of the ligament port 30 meets the ball 22 surface. The port could therefore be blind, or could exit through the femoral neck 24, or a portion of the ball 22 that does not engage the cup, or through some other location on the femoral stem 26. Of course, a straight port 30 is easier to produce, because it can be made with a single drilling operation rather than involving casting or multiple drilling or complex machining operations.

The acetabular component 60 of the invention 10 includes a cup 62 having a hemispherical receptacle 64 to receive the ball 32 of the femoral component 20. The cavity of the hemispherical receptacle 64 of the acetabular component 60 is thus substantially the same size as or slightly larger than the ball 22 of the femoral component 20. The exterior surface 66 of the cup 62 generally defines a hemisphere larger than the hemispherical receptacle 64, so that the hemispherical receptacle 64 and the hemispherical exterior surface 66 define a cup wall 68 therebetween.

The cup 62 is of a size and overall configuration that is generally utilized in the art. It is preferably fabricated from a biocompatible material having a low coefficient of friction, such as polyethylene or other polymers or composites of the same, in order to allow smooth sliding between the hemispherical receptacle 64 of the acetabular component 60 and the ball 22 of the femoral component 20.

The cup 62 includes an acetabular component ligament port 70 extending from the hemispherical receptacle 64 through the cup wall 68 to the exterior surface 66. As in the case of the femoral component ligament port 30, the acetabular component ligament port 70 is shown straight and through the cup wall 68 in the preferred embodiment of FIG.

1, but could be in some other design as well such as a blind hole or a non-linear hole so long as there is an opening to the hemispherical receptacle 64.

A ligament 80 extends from the exterior surface 66 of the cup 62 through the acetabular component ligament port 70 and into the hemispherical receptacle 64. From there, the ligament extends through the femoral component 20 ball 22, the femoral neck 24 and femoral stem 26, via the femoral component ligament port 30. A free end 82 of the ligament 80 extends out the femoral component ligament port 30 adjacent the femoral stem 26.

As shown in FIG. 2, the acetabular end 84 of the ligament 80 is secured to the acetabulum via a fastener 88. The fastener 88 may be any device capable of attaching to the acetabulum such as a screw or an element capable of being cemented to the bony structure. The femoral end 82 of the ligamentous material 80 extends through a hole drilled in the femur and attaches to the femur. As in the case of the acetabular end 84 of the ligamentous material, the attachment is accomplished with a fastener 90 or other suitable means. Alternatively, the femoral end 82 of the ligament 80 could be attached to the femoral component 20 of the prosthesis, and the acetabular end 84 of the ligament 80 could be attached to the acetabular component 60 of the prosthesis, but such an arrangement allows tension on the ligament to urge the prosthesis components apart from the bony structure.

The ligament 20 may be of any biocompatible ligamentous material of sufficient strength and durability. In a preferred embodiment, the ligament 70 is polyester, Gortex or teflon.

Each of the ligament ports 30 and 70 are preferably chamfered in the manner shown in FIG. 1, on the ends opening to the opposite joint component. Thus the end 32 of the femoral component ligament port 30 which opens to the acetabulum 60 is chamfered. Similarly, the end 78 of the acetabular component ligament port 70 which opens to the femoral component 20 is chamfered. The chamfering facilitates the movement of the femoral ball 22 in the acetabulum cup 62 without binding the ligament 80, in the manner described below.

The assembled femoral component 20 and acetabular component 60 are shown in the side sectional view of FIG. 2. The ball 22 of the femoral component 20 is received by the hemispherical receptacle 64 of the acetabulum component 60. (Although the depictions of FIG. 2 and FIG. 3 show a gap between the ball 22 and the hemispherical receptacle 64, such gap is only for clarifying the drawings. It should be appreciated that the ball 22 in fact rests on and in contact with the surface of the hemispherical receptacle 64.) The femoral component 20 and acetabular component 60 are held together, to ensure that the ball 22 and hemispherical receptacle 64 remain engaged, by the ligament 80. The acetabular end 84 of the ligament 80 is fastened to the fastener 88 which in turn is fastened to the acetabulum. The free end 82 of the ligament 80 is formed into a knot or is otherwise secured in a manner that fixes the length of the ligament 80. By fixing the length of the ligament 80, the engagement between the ball 22 of the femoral component 20 and the hemispherical receptacle 64 of the acetabular component 60 is defined. A relatively long ligament which includes significant "play" will define a loose engagement; a shorter ligament with little or no play will define a more secure engagement; and a ligament under tension will define an even more secure engagement.

Another area for adaptation of the prothesis of the present invention to accommodate the specific needs of a patient relates to the positioning of the ligament port 30. It can be appreciated that the particular physiology of a patient my dictate a ligament port 80 position which urges the femoral component 20 toward the acetabular component 60 in a direction other than the particular direction depicted in the figures.

The present invention thus allows for considerable choice by the physician in defining the engagement between the femoral component 20 and acetabular component 60 of the prostheses and thus the overall flexibility allowed by the patient. In making this choice, the physician will likely consider the patent's age, lifestyle, medical history a nd overall health among other factors. The choice can be made prior to surgery, or can even be made in the course of sfirgery to allow consideration of physiological factors discovered at that time.

Another important benefit of She invention involves the system by which universal ball and socket type movement is allowed between the ball 22 of the femoral component 20 and the hemispherical receptacle 64 of the acetabulum component 60. FIG. 3 shows the femoral component 20 shifted downwardly and inwardly in relation to the acetabular component 60. Such a shift corresponds to the femur moving inward in the patient, as occurs for example when the patient's legs are crossed. It can be seen from FIG. 3 that this movement produces a counterclockwise rotation of the ball 22 in the hemispherical receptacle 64. This rotation shifts the surface of the ball 22 in relation to the surface of the hemispherical receptacle 64, thereby shifting the end 32 of the femoral component ligament port 30 in relation to the end 78 of the acetabular component ligament port 70.

Because the ports 30 and 70 are preferably larger in cross section than the ligament 80, this shifting is accommodated without binding the ligament between the ball 22 and the hemispherical receptacle 64 by the ligament shifting to the port wall nearest the port of the opposite component. Thus, as shown in FIG. 3, the ligament 80 shifts to the wall of the end 32 of the femoral component port 30 that is nearest the acetabular port 70, and the ligament 80 shifts to the wall of the end 78 of the acetabular component port 78 that is nearest the femoral port 30.

Additional movement can be accommodated between the ball 22 of the femoral component 20 in relation to the hemispherical receptacle 64 of the acetabular component 60, without binding the ligament 80 between the ball 22 and the hemispherical receptacle 64, by chamfering the port ends 32 and 78 in the manner shown in FIG. 3. Such chamfering serves to enlarge the port ends 32 and 78, thereby positioning a wall of each port end 32 and 78 closer to the port end of the opposite component. Thus, the chamfering of the end 32 of the femoral component port 30 positions a wall of that end 32 closer to the acetabular component port 70 upon rotation of the ball 22 within the hemispherical receptacle 64. Similarly, the chamfering of the end 78 of the acetabular component port 70 positions a wall of that end 78 closer to the femoral component port 30 upon rotation of the ball 22 within the hemispherical receptacle 64. By effectively positioning the wall of each port end closer to the port of the opposite component through the chamfer, the ball 22 can rotate further in relation to the hemispherical receptacle 64 without binding the ligament 80 between the two.

An additional advantage to the system of the present invention for maintaining engagement of the femoral component 20 with the acetabular component 60, is that the engagement force steadily increases as the movement of the femoral component 20 in relation to the acetabular component 60 increases. The engagement force is at its minimum when the femoral component 20 and acetabular component 60 are in a natural and relaxed position with perfect alignment between the femoral component port 30 and the acetabular component port 70, as shown in FIG. 2. Because the shortest distance between two points is a straight line, this alignment results in the least tension on and maximum "play" in the ligament 80. Rotation of the ball 22 in relation to the hemispherical receptacle 64 (and this movement of the femoral component 20 in relation to the acetabular component 60) is little resisted by the ligament 80. In contrast, the engagement force is greater when the femoral component 20 and acetabular component 60 are in a position shifted from the natural and relaxed position. As shown in FIG. 3, such a shift results in misalignment between the femoral component port 30 and the acetabular component port 70. This misalignment uses up the "play" in the ligament 80, or even tensions the ligament 80 depending on the degree of misalignment and the "play" in the ligament chosen by the physician. The result is that further movement of the femoral component 20 in relation to the acetabular component 60 to cause further rotation of the ball 22 in relation to the hemispherical component 64 in the direction of misalignment, is resisted by the ligament 80. The resistive force increases as the extent of movement increases, in a manner similar to the resistive force exerted by natural ligaments or a natural joint. Such a system is superior to prior art systems in which the resistive force is at a constant minimum over a wide range of movement, and then abruptly changes to a maximum where the neck 24 (see FIG. 1) of the femoral component 20 impinges on the edge of the cup 62 of the acetabular component 80. The system of the present invention helps to dissipate dislocating forces before they can rotate the ball 22 in relation to the hemispherical receptacle 64 sufficiently to impinge the neck 24 of the femoral component 20 on the edge of the cup 62 of the acetabular component 60. At the same time, however, the system allows ample flexibility when the femoral component 20 is in a natural and relaxed position in relation to the acetabular component 60.

The prostheses of the invention is implanted in a manner similar to the methods known in the art. An important departure in the surgical procedure, however, is the step of the fixing the ligament 80 onto the femur and acetabulum. As discussed above, this step can be performed prior to or during the surgery. The point is to fix the ligament 80 length to define the engagement between the femoral component 20 and the acetabular component 70. In a preferred embodiment, this entails screwing a fastener 88 for attachment to the acetabular end 84 of the ligament 80 into the bony structure of the acetabulum; cementing or press fitting the acetabular component 60 into place; drilling a hole through the femur; threading the ligamentous material 80 through the femur hole; and attaching the femur end 82 of the ligamentous material 80 to the femur.

An alternative embodiment of the present invention is depicted in FIG.4. The alternative embodiment includes a femoral component 120 and acetabular component 160. The femoral component includes a ball 122 attached to a neck 124 which joins a stem 126 in the manner of the embodiment of FIGS. 1–3. The acetabular component 160 includes a receptacle 164 to receive the ball 122 of the femoral component 120. The femur is shown in FIG. 4, as is a portion of the acetabulum bony structure.

The embodiment of FIG. 4 utilizes a ligament 180 on the exterior of the prosthesis to maintain engagement between the femoral component 120 and the acetabular component 160. The femoral end 182 of the ligament 180 is attached to the femur by a fastener 196 or by other suitable means, and the acetabular end 198 of the ligament 180 is attached to the acetabulum by another fastener 199 or other suitable attachment means.

It can be appreciated that the apparatus of FIG. 4 ensures engagement of the femoral component 120 with the acetabular component 160, because any dislocating movement of the ball 122 of the femoral component 120 from the receptacle 164 of the acetabulum component 160 is resisted by the ligament 180. Moreover, the greater the dislocating movement, the greater the resistive force.

Although a single ligament 180 is depicted in the embodiment of FIG. 4, the invention encompasses the use of multiple ligaments as well. For example, ligaments may be spaced around the joint whereby excessive rotation in any direction is resisted by at least one ligament. Such an arrangement could include a criss-crossing of the multiple ligaments or a web or networked design, or a positioning of the ligaments in a manner calculated to resist dislocating forces from particular directions.

We claim:

1. A hip prosthesis for implantation into a natural acetabulum and natural femur of a patient, comprising: a femoral component having a hemispherical portion and a femoral component hole in the hemispherical portion; an acetabulum component having a cup-shaped receptacle to receive the hemispherical portion to allow universal movement between the femoral component and acetabulum component, the acetabulum component having an acetabulum component hole in the cup-shaped receptacle; and a ligamentous material extending through the femoral component hole and the acetabulum component hole and adapted for attachment to at least the natural acetabulum to maintain engagement between the femoral component and acetabulum component.

2. The prosthesis of claim 1, wherein said femoral component hole includes a femoral component hole first port in the hemispherical portion and a femoral component hole second port not in the hemispherical portion, the femoral component hole extending from the femoral component hole first port to the femoral component hole second port.

3. The prosthesis of claim 2, wherein the femoral component hole is substantially straight.

4. The prosthesis of claim 3, wherein the ligamentous material extends through said femoral component hole and is engaged with femoral bone of the patient outside the femoral component hole.

5. The prosthesis of claim 2, wherein the acetabulum component hole includes an acetabulum component hole first port in the cup-shaped receptacle and an acetabulum component hole second port not in the cup-shaped receptacle, the acetabulum component hold extending from the acetabulum component hole first port to the acetabulum component hole second port.

6. The prosthesis of claim 5, wherein the ligamentous material extends through said acetabulum component hole and is engaged with acetabulum bone of the patient outside the acetabulum component hole.

7. The prosthesis of claim 1, wherein the femoral component hole includes a femoral component hole end in the hemispherical portion through which the ligamentous material extends, the femoral component hole end having a cross section larger than a cross section of the ligamentous material to allow lateral movement of the ligamentous material in the femoral component hole end.

8. The prosthesis of claim 7, wherein the femoral component hole end is chamfered.

9. The prosthesis of claim 1, wherein the acetabulum component hole includes an acetabulum component hole end in the cup-shaped portion through which the ligamentous material extends, the acetabulum component hole end having a cross section larger than a cross section of the ligamentous material to allow lateral movement of the ligamentous material in the acetabulum component hole end.

10. The prosthesis of claim 9, wherein the femoral component hole includes a femoral component hole end in the hemispherical portion through which the ligamentous material extends, the femoral component hole end having a cross section larger than a cross section of the ligamentous material to allow lateral movement of the ligamentous material in the femoral component hole end.

11. The prosthesis of claim 10, wherein at least one of the acetabulum component hole end and acetabulum component hole end is chamfered.

12. A hip prosthesis for implantation into an acetabulum and femur of a patient, comprising a femoral component having a hemispherical portion; an acetabulum component having a cup-shaped receptacle to receive the hemispherical portion; a femoral component hole in the femoral component, the femoral component hole having a port opening toward the acetabulum component, the port of the femoral component hole being chamfered to a diameter greater than a diameter of the femoral component hole; an acetabulum component hole in the acetabulum component; and a ligamentous material extending from the femoral component hole and out the femoral component hole port and into the acetabulum component to maintain engagement between the femoral component and the acetabulum component.

13. The prosthesis of claim 12, wherein the acetabulum component hole has a port opening toward the femoral component, the port of the acetabulum component hole being chamfered to a diameter greater than a diameter of the acetabulum component hole.

14. A hip prosthesis for implantation into an acetabulum and femur of a patient, comprising: a femoral component having a hemispherical portion; an acetabulum component having a cup-shaped receptacle to receive the hemispherical portion; an acetabulum component hole having a port opening toward the femoral component, the port of the acetabulum component hole being chamfered to a diameter greater than a diameter of the acetabulum component hole; a femoral component hole in the femoral component; and a ligamentous material extending from the acetabulum component hole and out the acetabulum component hole port and into the femoral component to maintain engagement between the femoral component and the acetabulum component.

* * * * *